(12) United States Patent
Miyatani et al.

(10) Patent No.: US 8,245,613 B2
(45) Date of Patent: Aug. 21, 2012

(54) THIN-SECTION MANUFACTURING APPARATUS

(75) Inventors: Tatsuya Miyatani, Chiba (JP);
Yukimitsu Kijima, Chiba (JP);
Masatoshi Nonoyama, Chiba (JP)

(73) Assignee: Sakura Finetek Japan Co., Ltd., Tokyo (JP)

( * ) Notice: Subject to any disclaimer, the term of this patent is extended or adjusted under 35 U.S.C. 154(b) by 342 days.

(21) Appl. No.: 12/548,089

(22) Filed: Aug. 26, 2009

(65) Prior Publication Data

US 2010/0050839 A1   Mar. 4, 2010

(30) Foreign Application Priority Data

Aug. 29, 2008  (JP) ................................. 2008-222004

(51) Int. Cl.
*B26D 1/00* (2006.01)
*B26D 7/18* (2006.01)
*G01N 1/06* (2006.01)

(52) U.S. Cl. ............. 83/98; 83/112; 83/155.1; 83/915.5

(58) Field of Classification Search ................. 83/14–15, 83/169–171, 22, 915.5, 919, 713, 714, 412, 83/42, 167, 703, 409.2, 98, 155, 155.1, 112; 62/51.1, 320; 73/863.11; 700/109
See application file for complete search history.

(56) References Cited

U.S. PATENT DOCUMENTS

| | | | |
|---|---|---|---|
| 3,552,247 A | | 1/1971 | Pickett |
| 3,667,330 A | * | 6/1972 | Kobernick ........................ 83/98 |
| 3,733,948 A | * | 5/1973 | Pickett ............................... 83/98 |

(Continued)

FOREIGN PATENT DOCUMENTS

DE           4307738      *   9/1993

(Continued)

OTHER PUBLICATIONS

European Search Report for European Application No. 09168376.3, dated Dec. 29, 2009, 5 pages.

*Primary Examiner* — Laura M. Lee
(74) *Attorney, Agent, or Firm* — Brinks Hofer Gilson & Lione

(57) ABSTRACT

To provide a thin-section manufacturing apparatus capable of firmly receiving and transferring a thin-section made by sectioning an embedded block by bringing a transfer belt into a wet state, a thin-section manufacturing apparatus 1 includes a cutter 3 of sectioning an embedded block B, a cutter fixing portion 15 having a fixing base 16 of supporting the cutter 3 and an cutter holder 17 of squeezing the cutter 3 from an upper side, a sample base of fixing the embedded block B, feeding means 4 for moving the sample base 2 relative to the cutter 3 in a predetermined feeding direction X, a liquid bath 6 arranged on a rear side of a cut edge 3a of the cutter 3 for storing a liquid W, and a transfer belt 20 in an endless shape having a first turn back portion 20a provided on an upper side of the cutter 3 and a second turn back portion 20b provided at an inner portion of the liquid bath 6 for transferring a thin-section B1 to the liquid bath 6, an upper face of the cutter holder 17 is formed with a liquid storing portion 18 of storing the liquid W, and the first turn back portion 20a of the transfer belt 20 is arranged at an inner portion of the liquid storing portion 18.

6 Claims, 13 Drawing Sheets

U.S. PATENT DOCUMENTS

| | | | | |
|---|---|---|---|---|
| 5,156,019 A | * | 10/1992 | McCormick | 62/320 |
| 5,713,255 A | * | 2/1998 | Izvozichikov et al. | 83/24 |
| 5,740,708 A | * | 4/1998 | Tabone | 83/100 |
| 7,600,457 B2 | * | 10/2009 | Voneiff et al. | 83/307.1 |
| 7,677,289 B2 | * | 3/2010 | Hayworth et al. | 156/447 |
| 7,811,518 B2 | * | 10/2010 | Kokubo | 422/65 |
| 8,087,334 B2 | * | 1/2012 | Miyatani et al. | 83/112 |
| 2006/0248997 A1 | * | 11/2006 | Studer | 83/427 |
| 2007/0039435 A1 | * | 2/2007 | Kokubo | 83/13 |
| 2007/0157786 A1 | * | 7/2007 | Miyatani et al. | 83/651 |
| 2007/0204740 A1 | * | 9/2007 | Miyatani et al. | 83/919 |

FOREIGN PATENT DOCUMENTS

| | | |
|---|---|---|
| EP | 1882925 A2 | 1/2008 |
| JP | 06-323967 A | 11/1994 |
| JP | 2007-178287 A | 7/2007 |
| WO | WO2007023651 * | 3/2007 |

* cited by examiner

THIN-SECTION MANUFACTURING APPARATUS

RELATED APPLICATIONS

This application claims priority under 35 U.S.C. §119 to Japanese Patent Application No. JP2008-222004 filed on Aug. 29, 2008, the entire content of which is hereby incorporated by reference.

BACKGROUND OF THE INVENTION

1. Field of the Invention

The present invention relates to a thin-section manufacturing apparatus of making a thin-section by cutting an embedded block embedding a biological specimen taken out from the human body, a laboratory animal or the like.

2. Description of the Related Art

In a related art, as one of methods of inspecting and observing a biological specimen taken out from the human body, a laboratory animal or the like, there is known a method of observing the biological specimen by making a thin-section from an embedded block of embedding a biological specimen by an embedding material, thereafter, subjecting the thin-section to a staining. The thin-section made from the embedded block needs to be cut uniformly in a thickness of about 3 through 5 mm and without damaging the embedded biological specimen in order to enable a cell level observation. Therefore, an operation of making the thin-section from the embedded block as in the related art is entrusted to a manual operation by a skilled operator by using a thin edge cutter maintained in a sharpened state. On the other hand, for example, in a preclinical test, embedded blocks of several hundreds pieces per test are made, further, several sheets of the thin-sections per one embedded block are made. Therefore, the operator needs to make an enormous number of sheets of thin-sections, and therefore, in recent years, automation of a series of steps of making the thin-section has been desired.

As a thin-section manufacturing apparatus of automating making of the thin-section, there is proposed a constitution including a cutter of sectioning an embedded block, a feed mechanism of sectioning the embedded block by the cutter by moving a sample base of fixing the embedded block to the cutter, a belt mounted with the thin-section for transferring the thin-section, a direction switching portion provided on an upper side of the cutter substantially in parallel with a direction of a cut edge of the cutter proximately to the cut edge, a rear roller provided on a rear side of the cutter, and a liquid bath filled with water on the rear side of the cutter and dipped with a portion of the transfer belt (refer to, for example, Japanese patent publication No. JP-A-2007-178287).

Further, according to the biological specimen thin-section manufacturing apparatus, the transfer belt is traveled while sectioning the embedded block by the cutter. Thereby, the thin-section made from the embedded block is received by the transfer belt and transferred up to the liquid bath on the rear side, detached from the transfer belt and floated on water of the liquid bath. Here, the transfer belt is a belt in an endless shape which is always maintained in a wet state by passing an inner portion of the water of the liquid bath, thereby, the transfer belt is made to be able to receive the thin-section by a surface tension of water.

However, according to the apparatus disclosed by Japanese patent publication No. JP-A-2007-178287, the transfer belt is dipped into water at the liquid bath on the rear side, brought into the wet state, thereafter, traveled to the front side and turned back to receive the thin-section. Therefore, water included in the transfer belt is dropped or perspirated during a time period of moving from the rear side arranged with the liquid bath to the front side of receiving the thin-section, and there is a case in which the transfer belt cannot be brought into the sufficiently wet state in receiving the thin-section.

SUMMARY OF THE INVENTION

The invention has been carried out in view of the above-described situation and provides a thin-section manufacturing apparatus capable of firmly receiving to transfer a thin-section made by sectioning an embedded block by a cutter by bringing a transfer belt into a wet state.

In order to resolve the above-described problem, the invention proposes the following means.

According to the invention, there is provided a thin-section manufacturing apparatus comprising a cutter sectioning an embedded block, a cutter fixing portion including a fixing base supporting the cutter, and an cutter holder squeezing the cutter from an upper side to the fixing base, a sample base fixing the embedded block, feeding means for moving the sample base relative to the cutter in a predetermined feeding direction and sectioning the embedded block by the cutter, a liquid bath arranged on a rear side of a cut edge of the cutter and storing a liquid, and a transfer belt in an endless shape having a first turn back portion provided on an upper side of the cutter and a second turn back portion provided at an inner portion of the liquid bath and transferring a thin-section sectioned from the embedded block to the liquid bath, wherein an upper face of the cutter holder of the cutter fixing base is formed with a liquid storing portion of storing the liquid, and wherein the first turn back portion of the transfer belt is arranged at an inner portion of the liquid storing portion.

According to the thin-section manufacturing apparatus according to the invention, the thin-section can be made by sectioning the embedded block by the cutter by fixing the embedded block to the sample base and moving the embedded block along with the sample base relative to the cutter in the predetermined feeding direction by the feeding means. At this occasion, the transfer belt in the endless shape can be traveled by being turned back at the first turn back portion and the second turn back portion, and the thin-section which is made can be received by the transfer belt turned back at the first turn back portion on the upper side of the cutter. Here, the transfer belt is dipped into the liquid of the liquid bath at the second turn back portion on the rear side, traveled to the front side by being turned back, dipped into the liquid of the liquid storing portion formed at the upper face of the cutter holder at the first turn back portion, thereafter, receives the thin-section. That is, the transfer belt can firmly receive and transfer the thin-section by being brought into a preferable wet state by passing the liquid storing portion immediately before receiving the thin-section.

Further, in the above-described thin-section manufacturing apparatus, it is further preferable that an interval between the first turn back portion of the transfer belt and a wall face on a side of the cut edge of the liquid storing portion is formed with a clearance such that a liquid surface of the stored liquid is inclined to form by a surface tension from an upper end of the wall face to a surface of the transfer belt mounted with the thin-section.

According to the thin-section manufacturing apparatus according to the invention, the liquid surface of the liquid stored from the upper end of the wall face on the side of the cut edge of the liquid storing portion to the surface of the transfer belt mounted with the thin-section is inclined to form, and therefore, the thin-section which is made is guided to the surface of the transfer belt by being adsorbed to the liquid surface. Therefore, the thin-section can be received and transferred by the transfer belt further firmly.

Further, in the above-described thin-section manufacturing apparatus, it is further preferable that the liquid storing portion includes supplying and discharging means for supplying and discharging the liquid.

According to the thin-section manufacturing apparatus according to the invention, the liquid can be supplied and discharged to and from the liquid storing portion by the supplying and discharging means, and therefore, the transfer belt can preferably be brought into the wet state by bringing an amount of the liquid stored to the liquid storing portion to an optimum state.

Further, in the above-described thin-section manufacturing apparatus, it is further preferable that the supplying and discharging means includes a supply pipe of supplying the liquid and a discharge pipe of discharging the liquid, and one of the supply pipe and the discharge pipe is arranged substantially at a center in a width direction of the transfer belt, and other thereof are respectively arranged on both sides in the width direction of the transfer belt.

According to the thin-section manufacturing apparatus according to the invention, a distance in the width direction of the transfer belt from supply to discharge can be shortened in the liquid storing portion by arranging one of the supply pipe and the discharge pipe substantially at the center in the width direction of the transfer belt and arranging other thereof on the both sides in the width direction. Therefore, the liquid can be supplied and discharged swiftly in the width direction of the transfer belt and the transfer belt can be brought into the wet state further uniformly in the width direction by the supplying and discharging means.

Further, in the above-described thin-section manufacturing apparatus, it is further preferable to further comprise a control portion that for supplying the liquid by a previously set necessary amount to the liquid storing portion by the supplying and discharging means in accordance with sectioning the embedded block by moving the sample base relative to the cutter by the feeding means, and discharging the liquid of the liquid storing portion by the supplying and discharging means in accordance with finishing to section the embedded block by the cutter and the feeding means.

According to the thin-section manufacturing apparatus according to the invention, the transfer belt can further preferably be brought into the wet state by always storing the liquid of an optimum amount at the liquid storing portion when the thin-section is received by controlling the supplying and discharging means by the control portion, supplying the liquid to the liquid storing portion by the necessary amount in accordance with making the thin-section by sectioning the embedded block, and discharging the liquid of the liquid storing portion in accordance with finishing to section the embedded block.

Further, in the above-described thin-section manufacturing apparatus, it is further preferable that the liquid stored at the liquid storing portion of the cutter holder is liquid including water, and a bottom face of the liquid storing portion is provided with a hydrophilicity.

According to the thin-section manufacturing apparatus according to the invention, the bottom face is provided with the hydrophilicity, and therefore, the liquid supplied to the liquid storing portion can be smoothly spread over to the total, and the transfer belt can further uniformly be brought into the wet state.

Further, in the above-described thin-section manufacturing apparatus, it is further preferable that the liquid stored in the liquid storing portion of the cutter holder is the liquid including water, and a wall face surrounding the liquid storing portion is provided with a hydrophobicity.

According to the thin-section manufacturing apparatus according to the invention, the wall face is provided with the hydrophobicity, and therefore, the liquid stored in the liquid storing portion can be prevented from overflowing to an outer side.

According to the thin-section manufacturing apparatus of the invention, the liquid storing portion is formed at the cutter holder, the first turn back portion of the transfer belt is arranged at the inner portion of the liquid storing portion, and therefore, the thin-section made by sectioning the embedded block by the cutter can firmly be received and transferred by bringing the transfer belt into the wet state.

DETAILED DESCRIPTION OF THE PREFERRED EMBODIMENTS

First Embodiment

Figure 1:
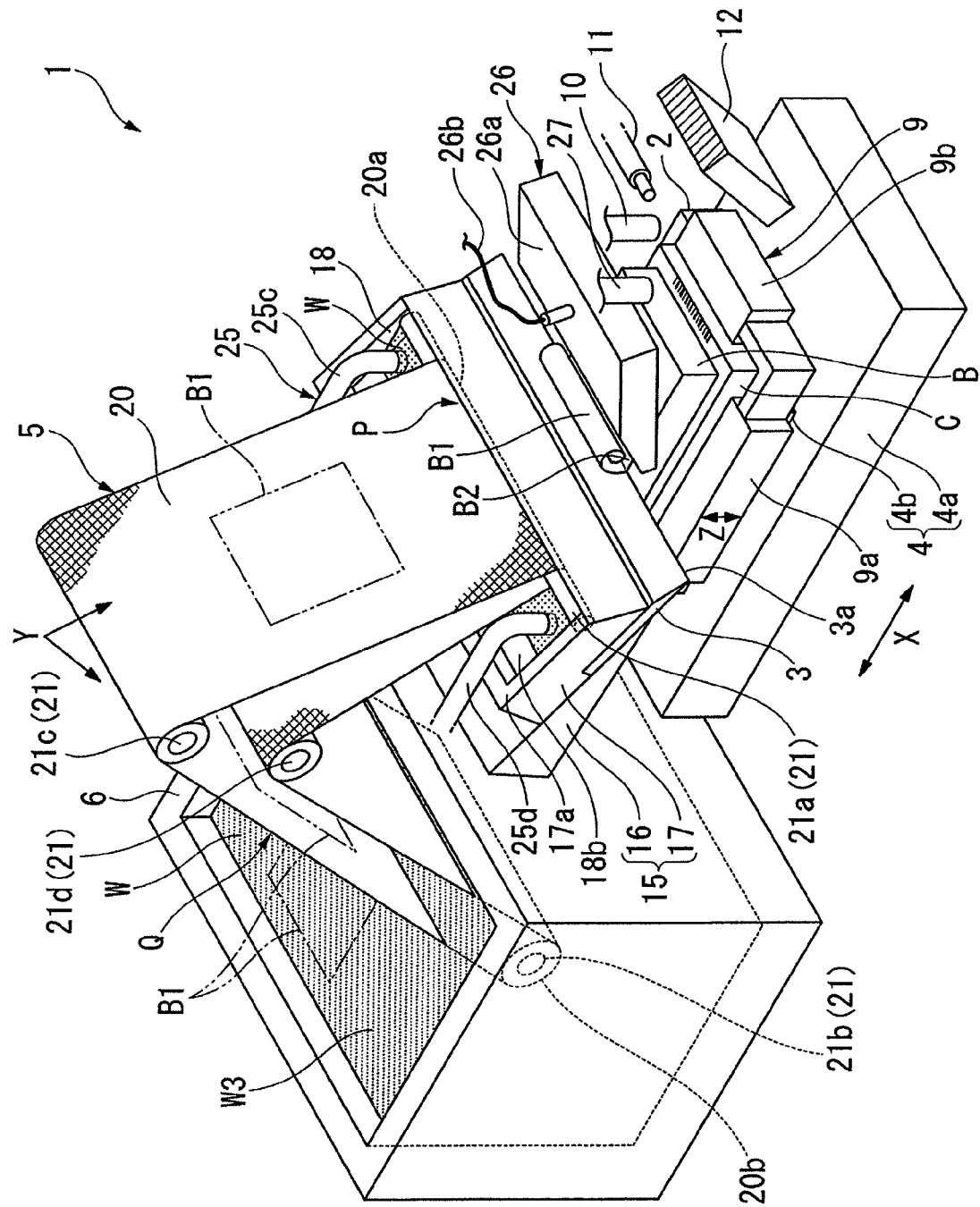
FIG. 1 is a total view showing a thin-section manufacturing apparatus of a first embodiment of the invention.
Figure 2:
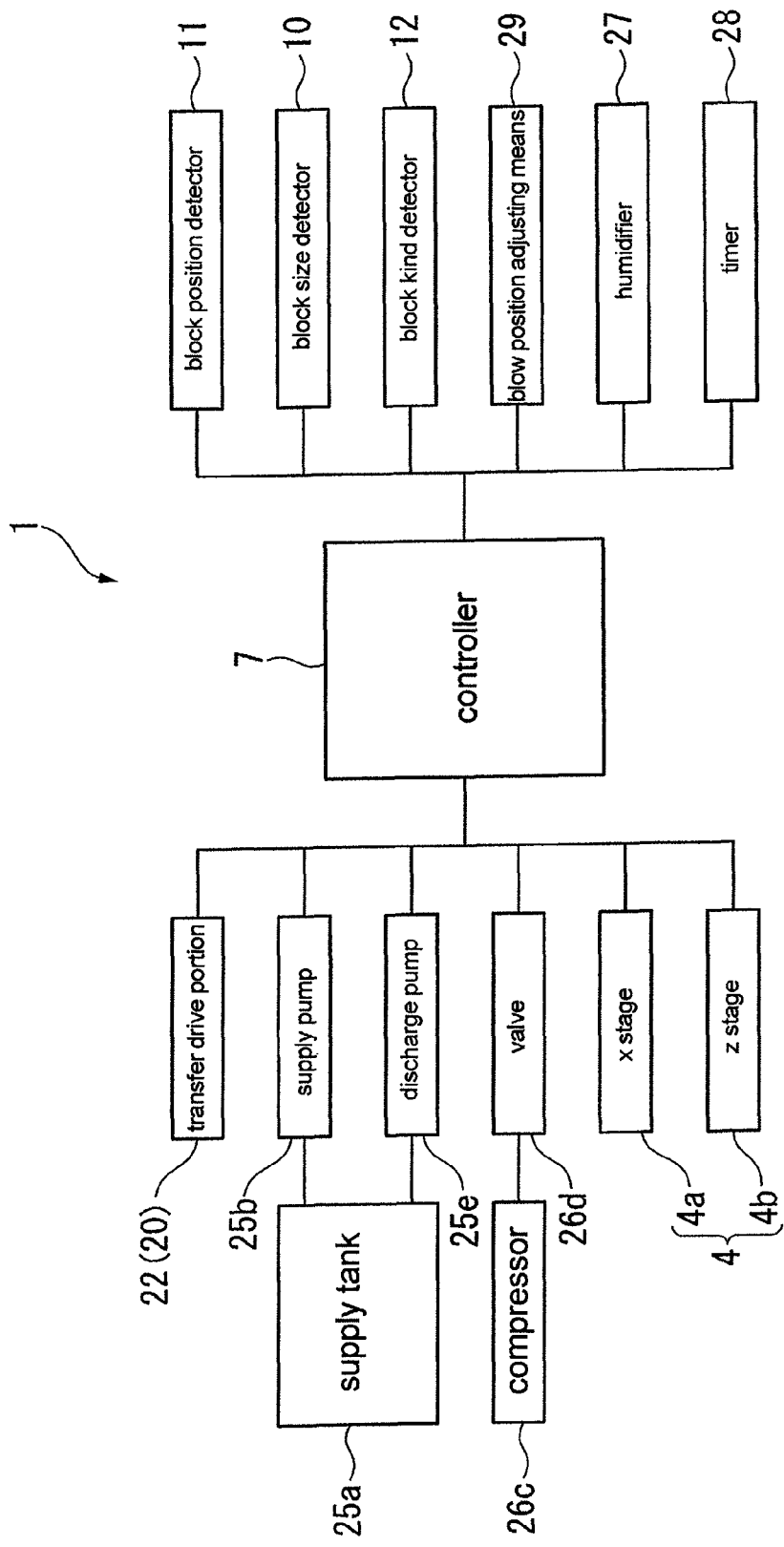
FIG. 2 is a block diagram showing the thin-section manufacturing apparatus according to the first embodiment of the invention.

FIG. 1 through FIG. 7 show a first embodiment according to the invention. A thin-section manufacturing apparatus 1 shown in FIG. 1 and FIG. 2 is an apparatus of automatically sectioning a thin-section from an embedded block B to transfer to successive steps in a procedure of making an extremely narrow thin-section having a thickness of about 3 through 5 μm from the embedded block B embedding a biological specimen, inspecting and observing the biological specimen included in the thin-section. The biological specimen is, for example, a tissue of an organ or the like taken out from the human body, a laboratory animal or the like, and is pertinently selected in a medical field, a pharmaceutical field, a food field, a biological field or the like. Further, the embedded block B embeds the above-described biological specimen by an embedding material, that is, covers to harden a surrounding thereof. Here, the embedding material is of a material which can easily be liquefied and cooled to solidify as described above, and is dissolved by being dipped in ethanol and is a resin, paraffin or the like. Further, the embedded block B is basically formed in a shape of a rectangular parallelepiped having a cut face B2 substantially in a rectangular shape, although in the embodiment, an explanation will be given of the embedded block B as being formed in the shape of the rectangular parallelepiped, the embedded block B is not necessarily limited in such a shape. The constitution of the thin-section manufacturing apparatus 1 will be explained as follows.

As shown by FIG. 1 and FIG. 2, the thin-section manufacturing apparatus 1 is provided with a sample base 2 of fixing a cassette C mounted with the embedded block B, a cutter 3 of sectioning the embedded block B, a feed mechanism 4 constituting feeding means of moving the sample base 2, transferring means 5 for transferring a thin-section B1 sectioned from the embedded block B by the cutter 3 along a predetermined transfer direction, a liquid bath 6 constituting thin-section receiving means for receiving the thin-section B1 transferred by the transferring means 5, and a controller 7 constituting a control portion of controlling respective constitutions. The sample base 2 is provided with a block fixing mechanism 9 of squeezing the cassette C mounted with the embedded block B from two directions by squeezing members 9a, 9b to fix and position.

The feed mechanism 4 includes an X stage 4a provided on a lower side of the sample base 2 for moving the embedded block B fixed to the sample base 2 in a feed direction X of sectioning the embedded block B, and a Z stage 4b of adjusting a position of the embedded block B in a thickness direction Z. Further, the controller 7 can move the sample base 2 in the feed direction X toward the cutter 3 by the X stage 4a at a constant feed speed, thereby, the embedded block B fixed to the sample base 2 can be sectioned by the cutter 3 at the feed speed. Further, the controller 7 can move the embedded block B in the thickness direction Z by a constant amount by the Z stage 4b, thereby, the embedded block B can be sectioned by the cutter 3 by a corresponding thickness.

Here, a block size detector 10 of detecting a size of the embedded block B, a block position detector 11 of detecting a position of the embedded block B, and a block kind detector 12 of detecting a kind of the embedded block B are provided at positions contiguous to the sample base 2. For example, the block size detector 10 is constituted by image taking means arranged on an upper side of the sample base 2, and analyzing means for analyzing an image from the image taking means, and by analyzing the image data of taking an image of the cut face B2 of the embedded block B, a length of a side along the feed direction X of the cut face B2 of the embedded block B, and a length of a side in a direction orthogonal thereto can be detected. The block position detector 11 detects a position of the embedded block B by, for example, laser light and can detect a position in the feed direction X of the embedded block B by irradiating the laser light to the embedded block B in the direction orthogonal to the feed direction X and detecting reflected light thereof. Further, the position of the embedded block B can also be detected by the image taking means of the above-described block size detector 10. Further, the block kind detector 12 is, for example, a bar code and two-dimensional bar code reader, and can detect the kind of the embedded block B mounted on the cassette C by reading the bar code and the two-dimensional bar code previously printed on the cassette C.

Figure 4:
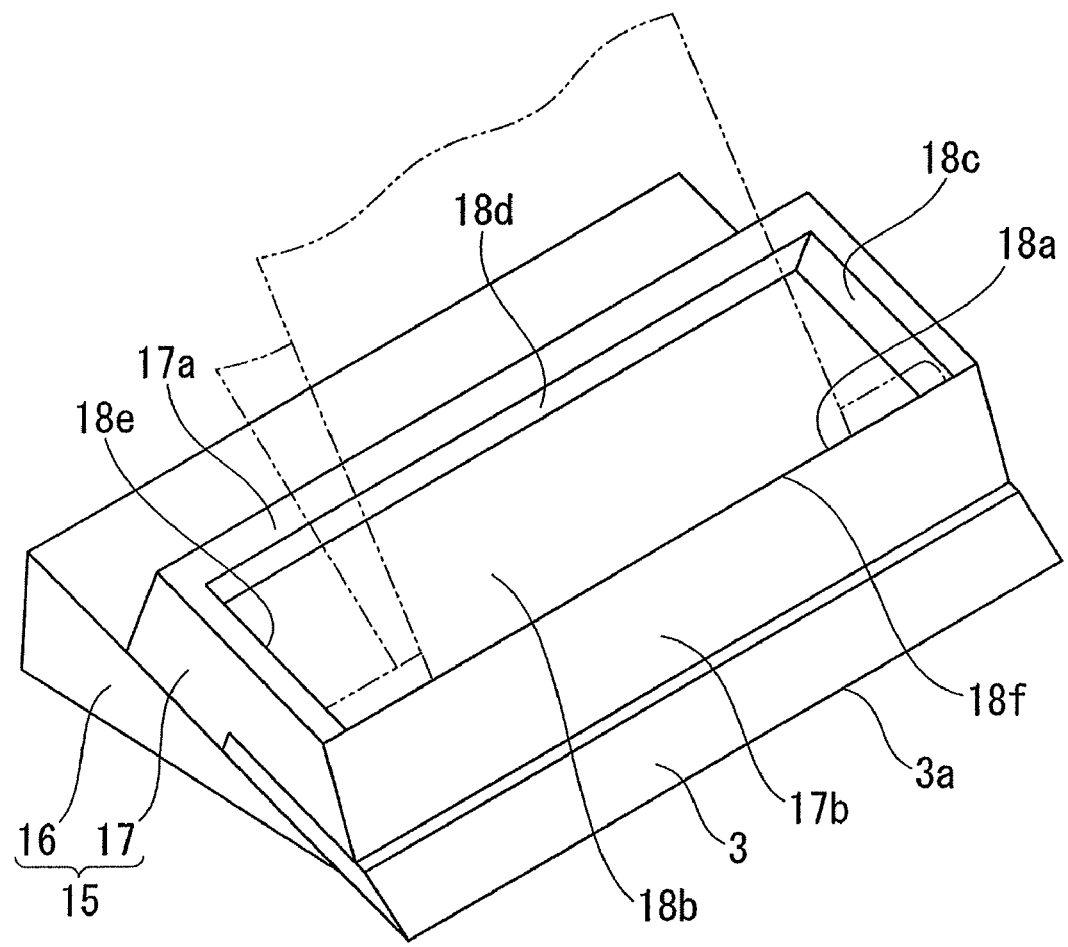
FIG. 4 is a perspective view showing details of a cutter fixing portion and the cutter according to the thin-section manufacturing apparatus of the first embodiment of the invention.

Further, the cutter 3 is fixed to a cutter fixing portion 15. The cutter fixing portion 15 includes a fixing base 16 of supporting a cut edge 3a of the cutter 3 by directing the cut edge 3a downward to be inclined by a predetermined angle, and a cutter holder 17 of squeezing the cutter 3 to the fixing base 16 from an upper side. Further, both ends of the fixing base 16 of the cutter fixing portion 15 are fixed to a frame constituting an outer contour of the apparatus, although not illustrated. Further, an upper face 17a of the cutter holder 17 is formed in a recessed shape as a liquid storing portion 18 and can store water W as a liquid by supplying and discharging means 25 as described later. Here, as shown by FIG. 4, the cutter holder 17 is subjected to a surface treatment constituting a hydrophobicity at an upper face 17a and a front face 17b facing a side of the cut edge 3a of the cutter 3 and inclined to correspond to an inclination of the cutter 3. Further, in the liquid storing portion 18 of the cutter holder 17, a surface treatment constituting a hydrophilicity is carried out at a bottom face 18b, and a surface treatment constituting a hydrophobicity is carried out at wall faces 18a, 18c, 18d, and 18e surrounding the bottom face 18b. The surface treatment of the hydrophilicity is carried out by, for example, forming a titanium oxide film. Further, the surface treatment of the hydrophobicity is carried out by, for example, coating fluororesin. Further, a material of forming the cutter holder 17 per se may be constituted by a material of the hydrophilicity or the hydrophobicity, and the surface treatment of the hydrophobicity or the hydrophilicity may be carried out only at a corresponding portion. Further, according to the embodiment, the cutter 3 is fixed to the cutter fixing portion 15 such that the cut edge 3a is orthogonal to the feed direction X of the embedded block B by the feed mechanism 4, that is, an explanation will be given by constituting a knife angle as 90 degrees.

Further, the liquid bath 6 constituting the thin-section receiving means is stored with, for example, water W as a liquid, and the thin-section can be delivered to a slide glass of a successive step by floating the thin-section B1 made from the embedded block B and transferred. Further, transferring means 5 includes a transfer belt 20 in the endless shape arranged from an upper side of the cutter 3 to an inner portion of the liquid bath 6 along a transfer direction Y, a roller group 21 of traveling the transfer belt 20, and a transfer drive portion 22 of driving to rotate a middle roller 21c constituting one of the roller group 21. Here, the transfer direction Y by the transfer belt 20 is set to be orthogonal to the cut edge 3a of the cutter 3 in a plane view thereof and according to the embodiment constituting the knife angle as 90 degrees, the transfer direction Y substantially coincides with the feed direction X in the plane view. In the embodiment, the transfer belt 20 is preferably formed by a mesh shape and particularly formed by a hydrophilic wire member to make water W easy to impregnate thereto.

Figure 3:
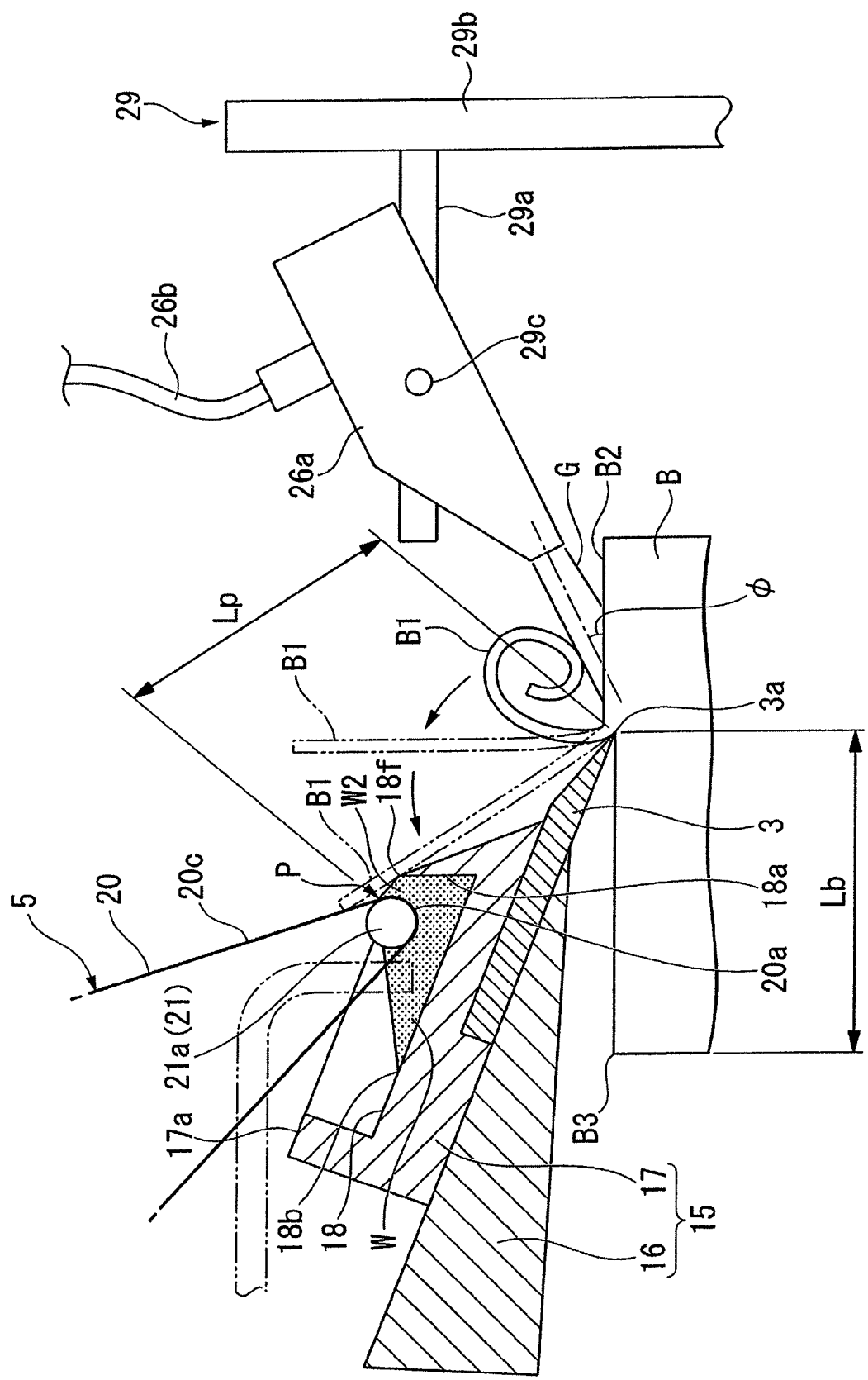
FIG. 3 is a sectional view showing details of a vicinity of a cutter of the thin-section manufacturing apparatus according to the first embodiment of the invention.

The roller group 21 includes a direction switch roller 21a of turning back the transfer belt 20 as a first turn back portion 20a on a side of being proximate to the cutter 3, a rear roller 21b provided at an inner portion of the liquid bath 6 constituting a rear side of the cut edge 3a of the cutter 3 for turning back the transfer belt 20 as a second turn back portion 20b, and middle rollers 21c, 21d of changing an angle of the transfer belt 20 between the direction switch roller 21a and the rear roller 21b. The direction switch roller 21a is rotatably supported by the cutter holder 17 by containing at least a portion thereof at an inner portion of the liquid storing portion 18 to be substantially in parallel with the direction of the cut edge 3a of the cutter 3. Further, as shown by FIG. 3, the transfer belt 20 is turned back to an upper side at the first turn back portion 20a by being wound around the direction switch roller 21a from a lower side and can receive the thin-section B1 sectioned by the cutter 3 by constituting a receive position P by a position of turning back to the upper side by the first turn back portion 20a. Further, the direction switch roller 21a is contained at the inner portion of the liquid storing portion 18 as described above, and therefore, in a state of storing water W at the liquid storing portion 18, the transfer belt 20 turned back by the first turn back portion 20a can be brought into a wet state by water W of the liquid storing portion 18.

Here, as shown by FIG. 3, a distance of separating the direction switch roller 21a and a wall face 18a on the side of the cut edge 3a of the liquid storing portion 18 is preferably as small as possible since when the distance becomes large, the transfer belt 20 is separated from the thin-section B1 sectioned from the embedded block B and extended to the receive position P. On the other hand, when the transfer belt 20 is brought into contact with the wall face 18a of the liquid storing portion 18, traveling of the transfer belt 20 is hampered, further, water W of the liquid storing portion 18 is not spread to a side of the wall face 18a, and therefore, it is preferable that the direction switch roller 21a is slightly separated from the wall face 18a. Particularly, although depending on a kind of a liquid stored in the liquid storing portion 18 and a material of the transfer belt 20, by setting the transfer belt 20 and the wall face 18a to a predetermined clearance, a liquid surface W2 of the stored liquid is formed to be inclined from an upper end 18f of the wall face 18a to a surface 20c mounted with the thin-section B1 of the transfer belt 20 by a surface tension, and the thin-section B1 can be adsorbed to guide by the liquid surface W2, and therefore, the constitution is further preferable.

Further, as shown by FIG. 1, the rear roller 21b is rotatably supported by the liquid bath 6 and dipped to water W constituting the liquid stored to the liquid bath 6 at the inner portion of the liquid bath 6. Therefore, an upper side of the transfer belt 20 traveling to the liquid bath 6 while mounting the thin-section B1 can be traveled to the first turn back portion 20a by being turned back to a lower side by constituting the second turn back portion 20b by the rear roller 21b. Further, the transfer belt 20 is dipped into water W at an inner portion of the liquid bath 6 at a vicinity of the second turn back portion 20b and can deliver the thin-section B1 to water W by constituting a delivery position Q by a position thereof brought into contact with a liquid surface W3.

Further, the controller 7 can travel the transfer belt 20 by three kinds of speeds of a receive speed, a transfer speed, and a delivery speed as described later by controlling the transfer drive portion 22. Here, the receive speed is a speed of the transfer belt 20 when the made thin-section B1 is received by the transfer belt 20 at the receive position P. The receive speed is set in accordance with a feed speed by the X stage 4a of the feed mechanism 4, and set to be substantially equal to the feed speed, or set to be slower than the feed speed within a range up to about 50% of the feed speed in the embodiment in which the knife angle of the cut edge 3a is 90 degrees. Further, the transfer speed is a speed when the made thin-section B1 is transferred by the transfer belt 20 and is set to a speed faster than the receive speed. Further, the delivery speed is a speed when the thin-section B1 is delivered from the transfer belt 20 to water W at the inner portion of the liquid bath 6 and is set to a speed slower than the transfer speed. Further, although the transfer speed may be constituted by a speed which differs by the receive speed, the transfer speed may be set to a constant value by constituting a speed sufficiently larger than the receive speed which varies in accordance with the feed speed, and also the delivery speed may be constituted by a constant value in accordance therewith.

Further, the thin-section manufacturing apparatus 1 of the embodiment further includes the supplying and discharging means 25 for supplying and discharging water W constituting the liquid to and from the liquid storing portion 18, gas blowing means 26 for blowing a compressed gas G to the thin-section B1 which is going to be made from the embedded block B, a humidifier 27 of humidifying the embedded block B, and a timer 28 of measuring time of driving respective mechanisms or the like. The supplying and discharging means 25 includes a supply tank 25a of supplying water W, a supply pump 25b of scooping up water W from the supply tank 25a, a supply pipe 25c opened at the liquid storing portion 18 for supplying water W from the supply pump 25b, a discharge pipe 25d opened at the liquid storing portion 18, and a discharge pump 25e of sucking water W at the inner portion of the liquid storing portion 18 to the supply tank 25a by way of the discharge pump 25d. The supply pipe 25c is provided to be contiguous to one side in a width direction of the transfer belt 20, and the opening is provided to constitute a side of the cut edge 3a at the inner portion of the liquid storing portion 18. Further, the discharge pipe 25d is provided to be contiguous to other side in the width direction of the transfer belt 20, and the opening is similarly provided to constitute the side of the cut edge 3a at the inner portion of the liquid storing portion 18. Further, a flow rate or drive time by the supply pump 25b and the discharge pump 25e is controlled by the controller 7.

Further, the gas blowing means 26 includes a blow nozzle 26a oppositely arranged on a front side of the cut edge 3a of the cutter 3, a compressor 26c connected to the blow nozzle 26a by way of a gas blow pipe 26b for generating compressed air as the compressed gas G, and a valve 26d provided at the gas blow pipe 26b for adjusting a flow rate of the compressed gas G. The blow nozzle 26a includes a slender opening arranged substantially in parallel with the cut edge 3a, and is arranged to be able to blow the compressed gas G in a direction of being directed to the cut edge 3a and at a position of being separated from the cut edge 3a above the cut face B2 of the sectioned embedded block B. Further, an amount of opening and closing the valve 26d is controlled by the controller 7. Further, as shown by FIG. 3, the blow nozzle 26a is provided with blow position adjusting means 29 for adjusting the position of the blow nozzle 26a. The blow position adjusting means 29 includes a distance adjusting portion 29a of adjusting the position toward a front and rear direction of the cut edge 3a, a height adjusting portion 29b of adjusting a height from the cut face B2 of the embedded block B, and an angle adjusting portion 29c of adjusting a blow angle Φ of the compressed gas G blown out from the blow nozzle 26a. Further, position adjustment of the blow nozzle 26a by the blow position adjusting means 29 is controlled by the controller 7. Further, the humidifier 27 can blow a gas in a mist state to the cut face B2, and can be arranged on an upper side of the cut face B2 as necessary under control of the controller 7 by a moving mechanism, not illustrated.

Further, the controller 7 includes a memory although not illustrated and the memory is stored with sectioning conditions for sectioning various kinds of embedded blocks as table data. Specifically, as the sectioning conditions, a kind of a biological specimen embedded in the embedded block B, and, in correspondence with the size of the embedded block B, a number of times of face matching, a sectioned thickness, a necessary humidifying amount in sectioning, a sectioning speed, that is, the feed speed in the feed direction X by the feed mechanism, as well as position conditions of the blow nozzle 26a in the gas blowing means 26 (a distance directed in the front and rear direction of the cut edge 3a, the height from the cut face B2, the angle of blowing the compressed gas G and the like), and pressure, time, timings of starting and finishing to blow the compressed gas G and the like are pointed out. Further, the controller 7 makes the thin-section B1 from the embedded block B by controlling respective constitutions in accordance with the sectioning conditions determined from the table data in accordance with the kind and size of the embedded block. An operation by the thin-section manufacturing apparatus 1 will be explained as follows.

Figure 5:
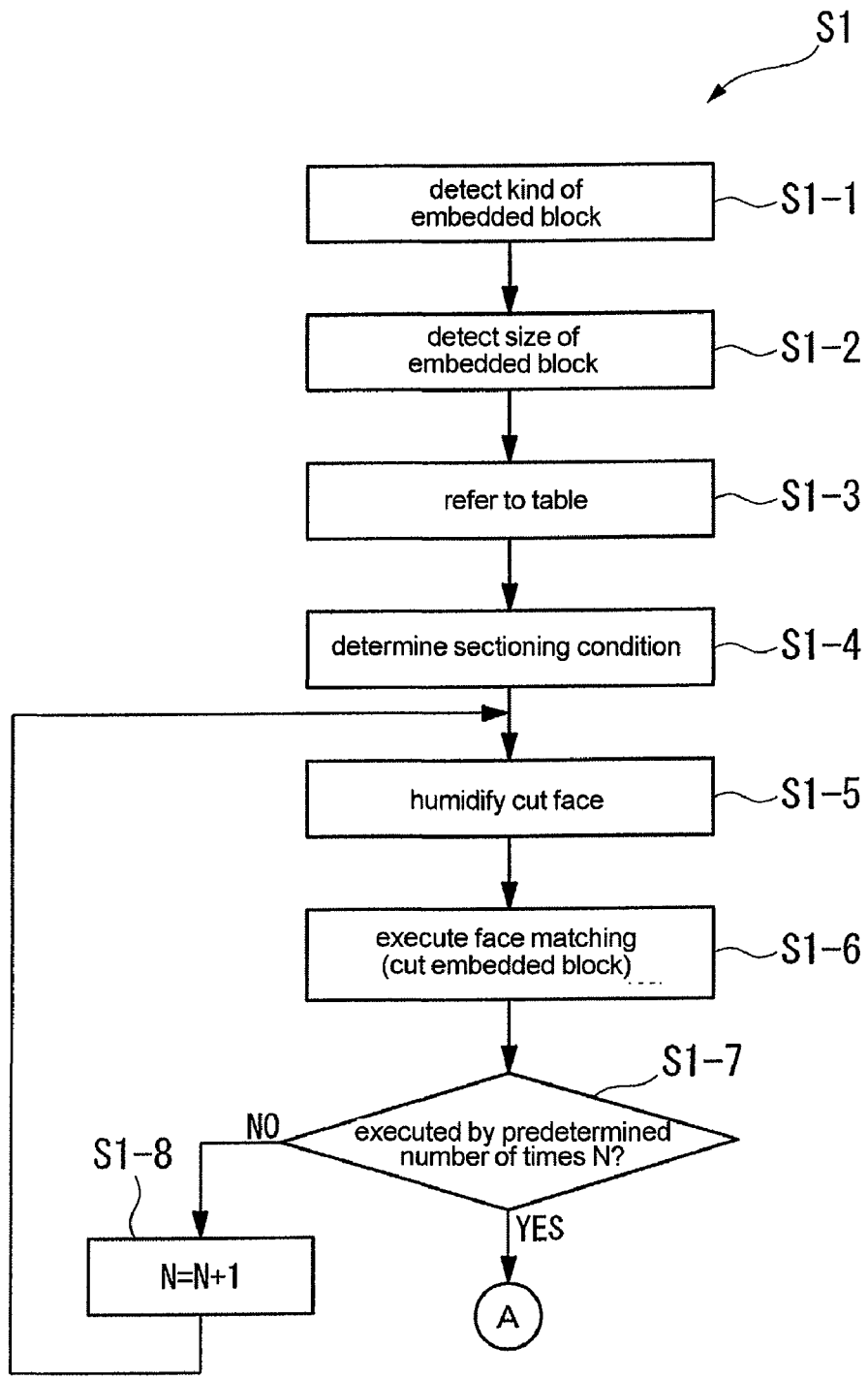
FIG. 5 is a flowchart showing details of preparing steps in making the thin-section by using the thin-section manufacturing apparatus according to the first embodiment of the invention.
Figure 6:
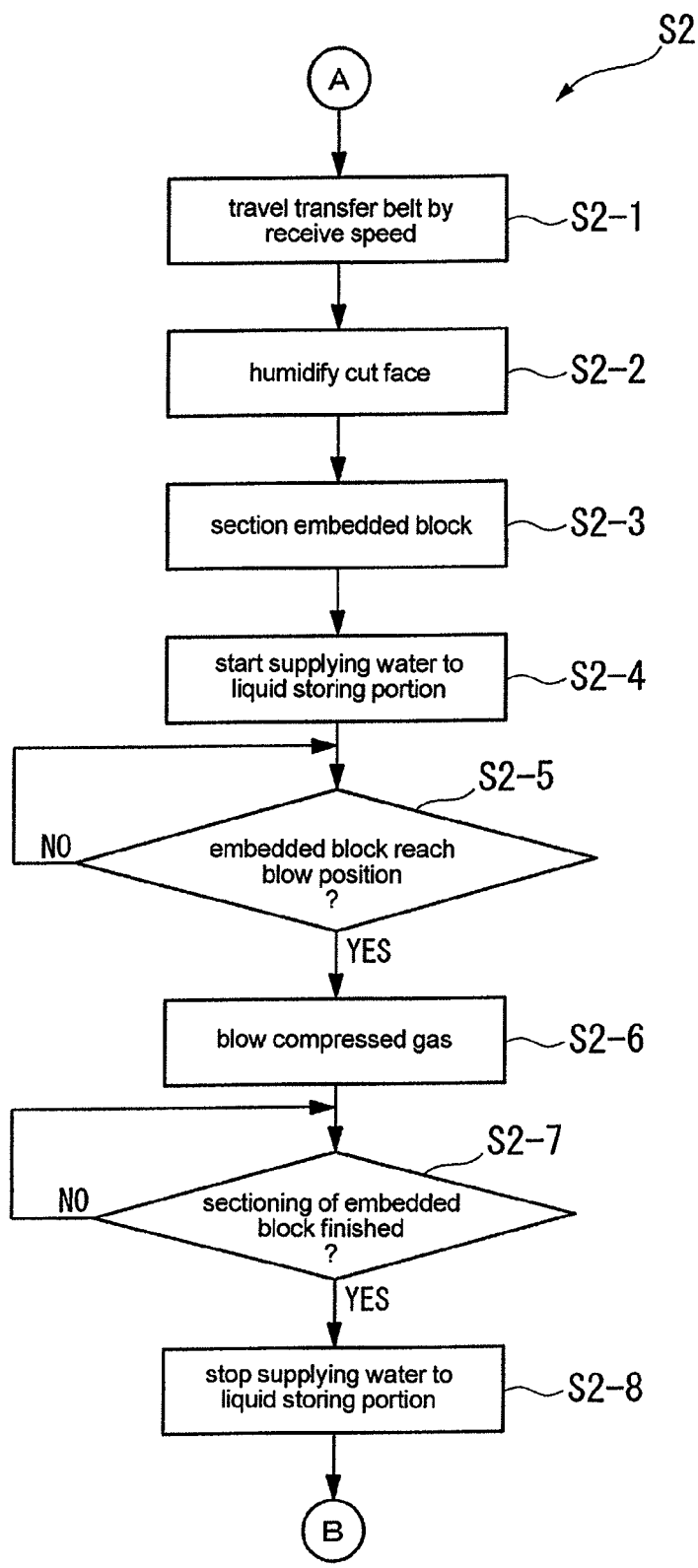
FIG. 6 is a flowchart showing details of thin-section manufacturing steps in making the thin-section by using the thin-section manufacturing apparatus according to the first embodiment of the invention.
Figure 7:
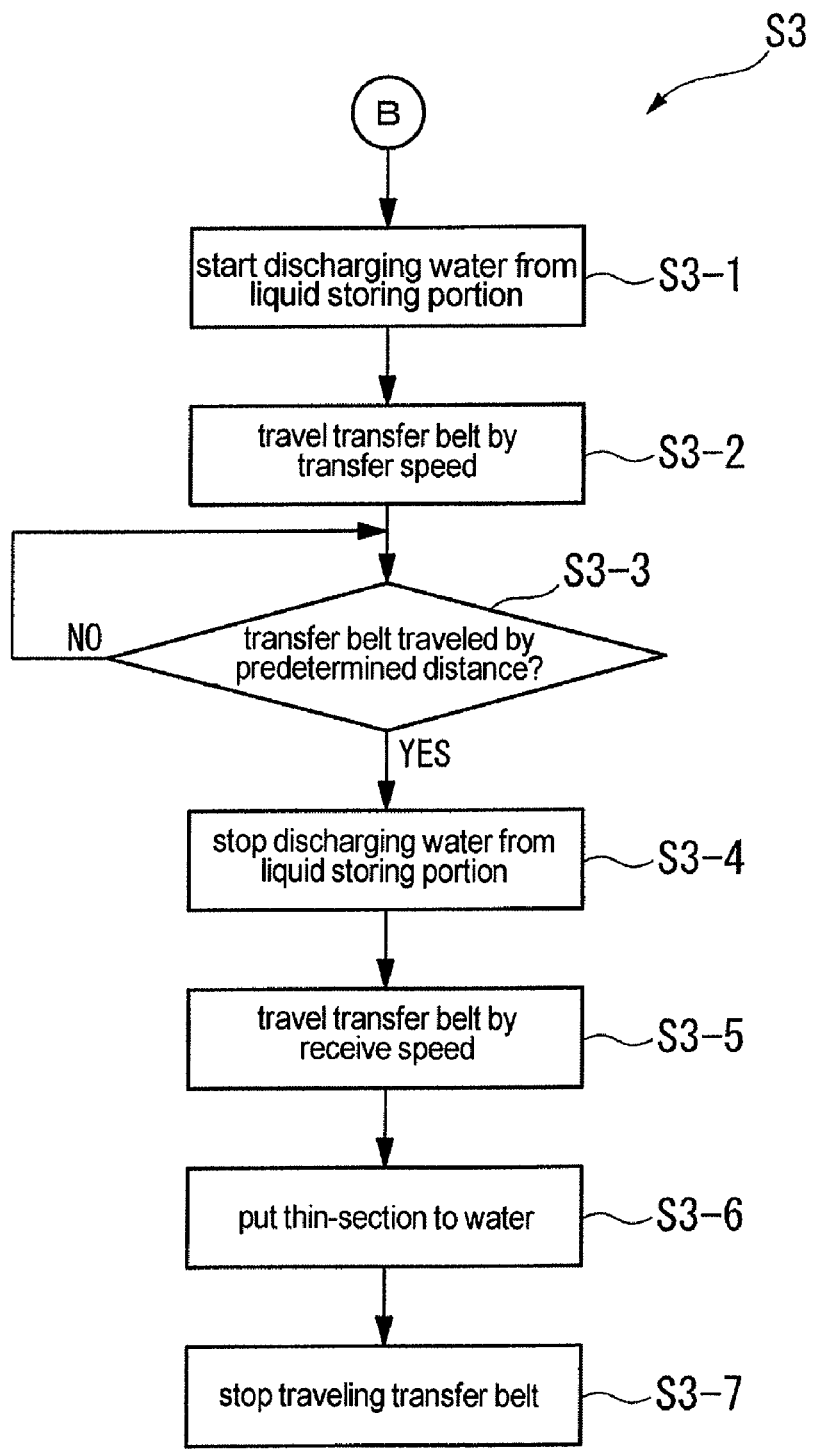
FIG. 7 is a flowchart showing details of transferring steps in fabricating the thin-section by using the thin-section manufacturing apparatus according to the first embodiment of the invention.

FIG. 5 through FIG. 7 show a flow of making and transferring a thin-section based on the control by the controller 7. First, the following operation is carried out based on a flow shown in FIG. 5 as a preparing step S1. When the cassette C mounted with the embedded block B is mounted to the sample base 2 and is fixed by the block fixing mechanism 9, the block kind detector 12 detects the kind of the embedded block B mounted to the cassette C from information printed on the cassette C, and inputs the kind to the controller 7 as kind data (step S1-1). Next, the block size detector 10 detects the size of the embedded block B and inputs the size to the controller 7 as size data (step S1-2). Next, the controller 7 refers to a table stored to the memory, not illustrated (step S1-3), and determines the sectioning conditions in correspondence with the inputted kind data and the inputted size data (step S1-4).

Further, face matching is carried out successively. That is, first, the controller 7 humidifies the cut face B2 of the embedded block B based on the necessary humidifying amount constituting one of the previously determined sectioning conditions by driving the humidifier 27 (step S1-5). Next, the controller 7 cuts the embedded block B as face matching (step S1-6). That is, first, the controller 7 moves the embedded block B in the thickness direction Z by a corresponding amount by driving the Z stage 4b of the feed mechanism 4 based on the thickness to be sectioned constituting the previously determined sectioning condition. Next, the controller 7 moves the embedded block B in the feed direction X toward the cutter 3 by driving the X stage 4a constituting the feed mechanism based on the sectioning speed determined as one of the sectioning conditions. Thereby, the embedded block B is sectioned by the thickness and the speed which are determined previously as the sectioning conditions. Further, a cut chip of the embedded block B in the face matching is abandoned by being recovered by recovering means on a lower side although not illustrated. Next, the controller 7 determines whether a number of times of the face matching reaches a number of times N which is previously determined as the sectioning condition (step S1-7). In this case, the number of times is still one time, and therefore, it is determined that the number of times N is not reached, numeral 1 is added to the current number of times 1 (step S1-8), the face matching from step S1-5 is repeatedly carried out again. Further, when it is determined that the face matching is carried out by the number of times N at step S1-7, the controller 7 proceeds to next thin-section manufacturing step S2 and carries out a flow shown in FIG. 6.

That is, as shown by FIG. 6, first, the controller 7 travels the transfer belt 20 by the receive speed by driving the transfer drive portion 22 of the transferring means 5 (step S2-1). Here, as described above, the receive speed is determined in correspondence with the feed speed in the feed direction X by the X stage 4a of the feed mechanism 4, for example, according to the embodiment, the controller 7 drives the transfer drive portion 22 by determining the receive speed to be 60% of the feed speed based on the feed speed constituting the sectioning speed constituting one of the determined sectioning conditions. Next, the controller 7 humidifies the cut face B2 of the embedded block B after finishing the face matching by the necessary humidifying amount which is determined again by driving the humidifier 27 (step S2-2).

Next, sectioning of the embedded block B is carried out (step S2-3). That is, first, the controller 7 moves the embedded block B in the thickness direction Z by the corresponding amount by driving the Z stage 4b of the feed mechanism 4 based on the thickness to be sectioned which is determined as one of the sectioning conditions. Next, the embedded block B is moved in the feed direction X toward the cutter 3 by driving the X stage 4a of the feed mechanism based on the sectioning speed which is determined as one of the sectioning conditions. Thereby, the embedded block B is successively sectioned and the thin-section B1 is made by the thickness and the sectioning speed which are previously determined as the sectioning conditions. Further, although according to the embodiment, an explanation has been given without distinguishing the thicknesses and speeds to be sectioned between in the face matching and in making the thin-section, the thicknesses and the speeds in the two steps may be made to differ from each other.

Further, in accordance with sectioning the embedded block B at step S2-3, the controller 7 supplies water W from the supply pipe 25c to the liquid storing portion 18 of the cutter holder 17 by driving the supply pump 25b of the supplying and discharging means 25 (step S2-4). Further, an amount of supplying water W to the liquid storing portion 18 is previously set in accordance with a capacity of the liquid storing portion 18, and the controller 7 makes the liquid surface W2 set to the upper end 18f of the wall face 18a on the side of the cut edge 3a of the liquid storing portion 18 as shown by FIG. 3 by supplying water W by corresponding time and the previously set flow rate based on a result of measurement by the timer 28. Here, according to the embodiment, the bottom face 18b of the liquid storing portion 18 is subjected to the hydrophilic surface treatment, and therefore, water W supplied from the supply pipe 25c on one end side of the transfer belt 20 can be spread smoothly over a total thereof. On the other hand, the wall faces 18a, 18c, 18d, 18e surrounding the bottom face 18b are subjected to the hydrophobic surface treatment, and therefore, the stored liquid can be prevented from overflowing to an outer side. Further, from a positional relationship between the wall face 18a on the side of the cut edge 3a of the liquid storing portion 18 and the direction switch roller 21a, the liquid surface W2 of water W to be stored is formed to incline by the surface tension from the upper end 18f of the wall face 18a to the surface 20c of the transfer belt 20. Further, the transfer belt 20 which travels at the receive speed is turned back at the first turn back portion 20a and travels from the receive position P to the delivery position Q on the upper side by being brought into a wet state by passing water W of the liquid bath 6, further, by being brought into an optimum wet state by passing water W of the liquid storing portion 18. On the other hand, the controller 7 supplies water W by predetermined time and predetermined flow rate by driving the supply pump 25b, and after setting the liquid surface W2 disposed at the upper end 18f of the wall face 18a on the side of the cut edge 3a of the liquid storing portion 18, the controller 7 continuously supplies water W by a flow rate smaller than the previously set above-described flow rate. Therefore, even when water W of the liquid storing portion 18 successively adheres to the transfer belt 20 in accordance with traveling the transfer belt 20, an amount of water W of the liquid storing portion 18 can always be maintained constant.

Further, as step S2-5, in sectioning the embedded block B, the controller 7 monitors a position in the feed direction X of the embedded block B based on block position data detected and inputted by the block position detector 11. Further, when it is determined that the embedded block B reaches a previously set blow position, the controller 7 makes the compressed gas G blow from the blow nozzle 26a to the cut face B2 of the embedded block B by the pressure and the time which are previously determined as the sectioning conditions by the gas blowing means 26 (step S2-6). Further, the position of the blow nozzle 26a is adjusted based on the previously determined sectioning condition by the blow position adjusting means 29. Here, the blow position of the embedded block B is a position at which a length made as the thin-section B1 which is sectioned after starting sectioning by bringing a front end B3 of the embedded block B into contact with the cut edge 3a of the cutter 3, that is, a distant Lb from the front end B3 of the embedded block B to the cut edge 3a of the cutter 3 becomes equal to or larger than a distance Lp from the cut edge 3a of the cutter 3 to the receive position P, and according to the embodiment, the blow position is set as a position at which the both distances becomes substantially equal to each other.

Further, although in accordance with making the thin-section B1 gradually by sectioning the embedded block B, the thin-section B1 is curled by the thickness of making the thin-section B1 and a property of the embedded biological specimen, by blowing the compressed gas G to the cut face B2 of the embedded block B by the gas blowing means 26 at step S2-6, the compressed gas G is once blown onto the cut face of the embedded block, in a direction of being directed to the cut edge, further, at a position of being remote from the cut edge, thereafter, blown to the cut edge 3a by which the thin-section B1 is made along the cut face B2. Therefore, the compressed gas G is blown to the thin-section B1 which is made and extended from the cut edge 3a from a root portion thereof at which the cut edge 3a is disposed, and even when the thin-section B1 is curled, the compressed gas G is blown to an inner portion of the thin-section B1 in the curled shape. Therefore, even when the thin-section B1 is curled, the thin-section B1 is pushed to be spread from the inner portion showing the curled shape and can firmly be extended without being pushed to crush by the compressed gas G. Further, by carrying out blowing by the gas blowing means 26 when the embedded block B is disposed at the blow position, the front end of the extended thin-section B1 reaches the receive position P and is brought into contact with the transfer belt 20.

Therefore, the thin-section B1 is transferred from the receive position P to the delivery position Q along the transfer direction Y by receiving the made front end side by the transfer belt 20 while being made from the embedded block B. Here, the transfer belt 20 is brought into the wet state, and can be brought into the optimum wet state particularly by being dipped to water W of the liquid storing portion 18 immediately before the receive position P, and can firmly receive the thin-section B1 by an adsorption force of the wet water W. Further, according to the embodiment, the liquid surface W2 of water W of the liquid storing portion 18 is inclined to form by the surface tension from the upper end 18f of the wall face 18a to the surface 20c of the transfer belt 20, and therefore, the thin-section B1 is guided to the surface 20c of the transfer belt 20 by being adsorbed to the liquid surface W2, and the thin-section B1 can be received by the transfer belt 20 further firmly. Further, although there is a case in which in accordance with bringing the thin-section B1 into contact with the transfer belt 20, the thin-section B1 is brought into contact with also the front face 17b or the upper face 17a of the cutter holder 17, by being subjected to the hydrophobic surface treatment, it can be prevented that the transfer by the transfer belt 20 is hampered by sticking the thin-section B1 to the front face 17b or the upper face 17a.

Further, the front end side of the received thin-section B1 is successively transferred by the transfer belt 20, and a base end side thereof is further made from the embedded block B. At this occasion, the speed of the transfer belt 20 is set to the receive speed, and therefore, it can be prevented that the transferred front end side becomes faster than the speed of making the base end side and the thin-section B1 is pulled and torn off. Further, it can be prevented that the transferred front end side becomes excessively slower than the speed of making the base end side and the thin-section B1 made between the receive position P and the cut edge 3a of the cutter 3 is compressed to wrinkle.

Further, when the controller 7 monitors the block position data inputted from the block position detector 11 and determines that the embedded block B has passed the cut edge 3a of the cutter 3 as step S2-7, that is, when sectioning of the embedded block B is finished, the controller 7 stops driving the X stage 4a of the feed mechanism 4 and proceeds to step S2-8. At step S2-8, the controller 7 stops supplying water W to the liquid storing portion 18 by stopping to drive the supply pump 25b of the supplying and discharging means 25, and proceeds to a transferring step S3 to carry out a flow shown in FIG. 7.

That is, as shown by FIG. 7, first, the controller 7 discharges water W of the liquid storing portion 18 from the discharge pipe 25d by driving the discharge pump 25e of the supplying and discharging means 25 (step S3-1). Next, the controller 7 switches the speed of traveling the transfer belt 20 from the receive speed to the transfer speed by controlling the transfer drive portion 22 (step S3-2). Therefore, the thin-section B1 received by the transfer belt 20 is transferred swiftly to the delivery position Q at the transfer speed faster than the receive speed. Further, the controller 7 monitors a traveling distance from starting to travel the transfer belt 20 at step S2-1, determines whether the thin-section B1 is traveled by an amount of the previously set traveling distance to reach a vicinity of the delivery position Q (step S3-3) and when traveled by the amount of the traveling distance, the controller 7 stops discharging water W from the liquid storing portion 18 by the supplying and discharging means 25 (step S3-4), and switches the speed of traveling the transfer belt 20 from the transfer speed to the delivery speed by controlling the transfer drive portion 22 (step S3-5). Therefore, the thin-section B1 on the transfer belt 20 reaches the delivery position Q by the delivery speed, is touched to the liquid surface W3 of water W of the liquid bath 6 disposed at the delivery position Q, is detached from the transfer belt 20 and delivered to water W (step S3-6). Further, when the traveling distance of the transfer belt 20 becomes equal to or larger than the transfer distance from the receive position P to the delivery position Q, the controller 7 stops driving the transfer drive portion 22 and stops traveling the transfer belt 20.

As described above, according to the thin-section manufacturing apparatus 1 of the embodiment, the transfer belt 20 is dipped to water W of the liquid bath 6 at the second turn back portion 20b on the rear side, is turned back and travels to the front side, is dipped to water W of the liquid storing portion 18 formed at the upper face 17a of the cutter holder 17 at the first turn back portion 20a, thereafter, receives the thin-section B1. That is, the transfer belt 20 can be disposed at the receive position P by being brought into the preferable wet state by being brought into the wet state by the liquid bath 6 over the total and passing the liquid storing portion 18 immediately before receiving the thin-section B1, and can firmly receive and transfer the thin-section B1 at the receive position P. Further, according to the embodiment, water W stored in the liquid storing portion 18 is adjusted by being supplied and discharged by the supplying and discharging means 25 under the control by the controller 7. Therefore, when the thin-section B1 is received by the transfer belt 20, the thin-section B1 can be received by bringing the transfer belt 20 into the wet state further preferably by storing water W of the optimum amount always at the liquid storing portion 18.

Further, although according to the embodiment, at preparing step S1, the various sectioning conditions are determined by referring to the table data, all of the various sectioning conditions may be determined by manual input. Further, although at thin-section manufacturing step S2, the transfer belt 20 is traveled by the receive speed first at step S2-1, the invention is not limited thereto. The transfer belt 20 may be traveled by the receive speed until at least the distance Lb from the front end B3 of the embedded block B to the cut edge 3a by starting the sectioning, that is, the sectioned length becomes equal to the distance Lp from the cut edge 3a to the receive position P. Further, a timing of storing water W to the liquid storing portion 18 by the supplying and discharging means 25 at step S2-4 is not limited to that of the embodiment but water supply may be carried out at preparing step S1, and the supply may be finished until at least the front end of the thin-section B1 which is being made reaches the receive position P. Further, the control of the amount of supplying water W by the supplying and discharging means 25 is not limited to a control by time, but, for example, a liquid surface sensor may be provided at the liquid storing portion 18 and the control may be carried out thereby. Further, with regard to discharge of water W from the liquid storing portion 18 by the supplying and discharging means 25, although the discharge is carried out continuously until the thin-section B1 is transferred to the vicinity of the delivery position Q at step S3-3, when the discharge is finished, driving of the discharge pump 25e may be stopped at the time point. Further, when the amount of water W of the liquid storing portion 18 becomes the optimum amount in receiving the thin-section B1, the water may not necessarily be needed to discharge at every time.

Figure 8:
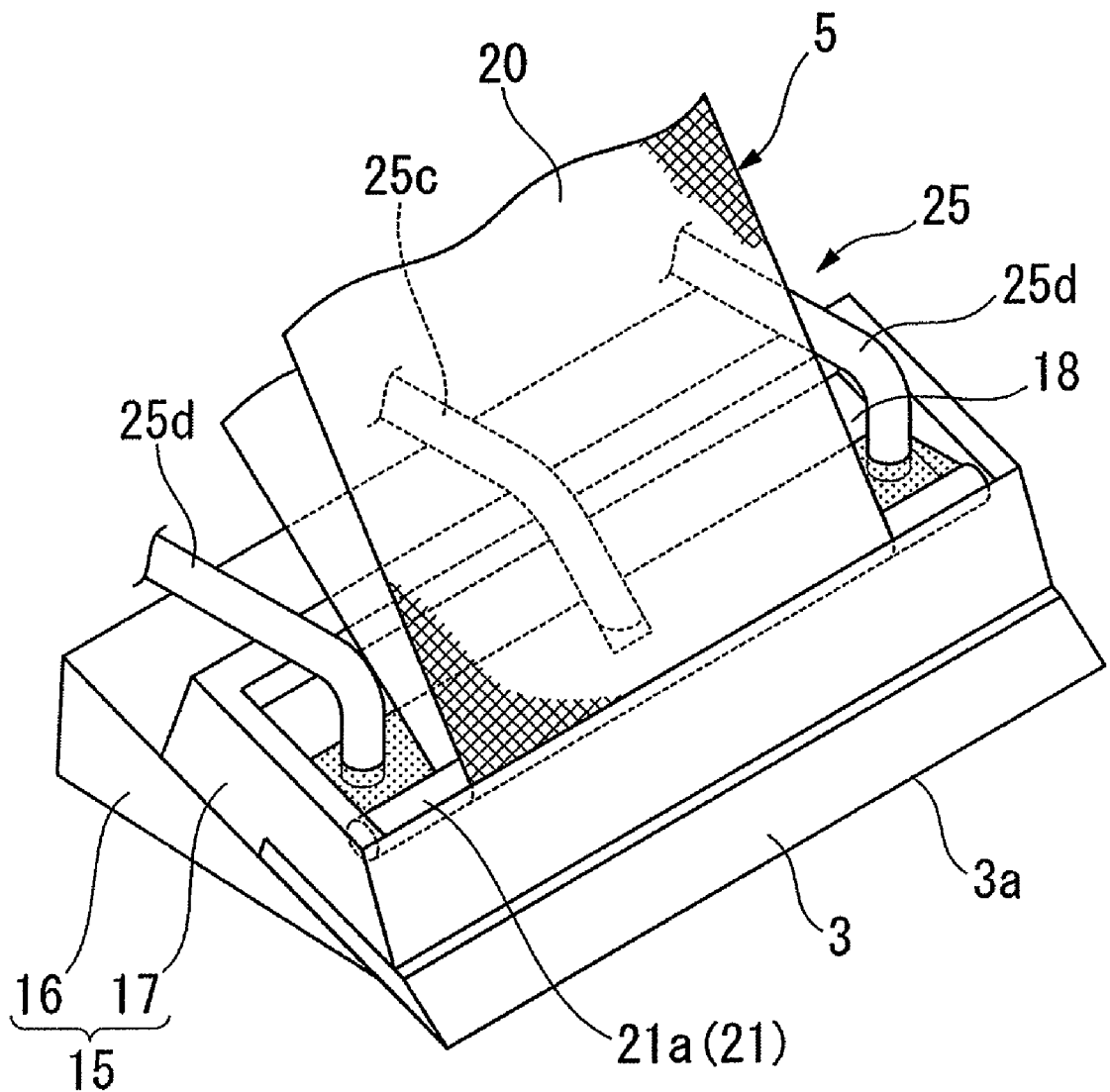
FIG. 8 is a perspective view showing details of supplying and discharging means of a thin-section manufacturing apparatus according to a first modified example of the first embodiment of the invention.
Figure 9:
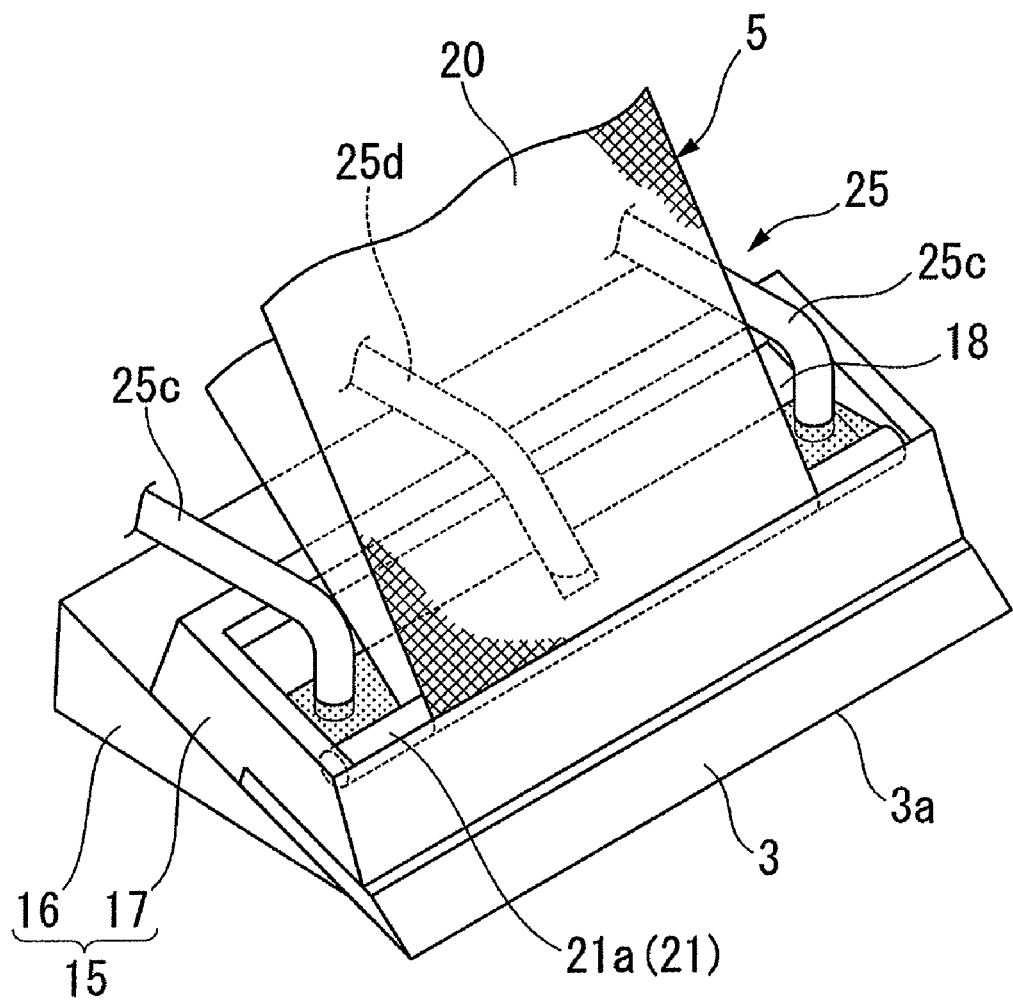
FIG. 9 is a perspective view showing details of supplying and discharging means of a thin-section manufacturing apparatus according to a second modified example of the first embodiment of the invention.
Figure 10:
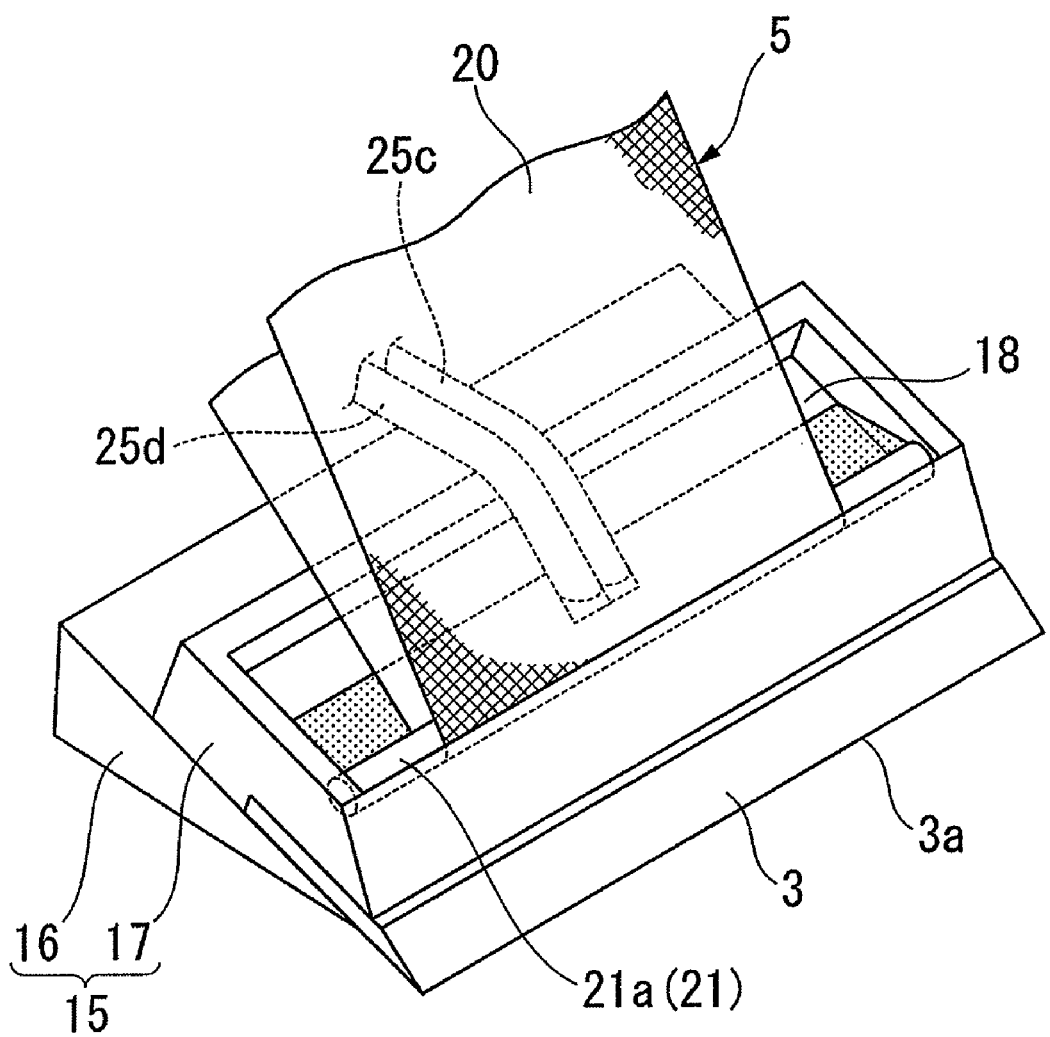
FIG. 10 is a perspective view showing details of supplying and discharging means of a thin-section manufacturing apparatus according to a third modified example of the first embodiment of the invention.

Further, although according to the embodiment, at the supplying and discharging means 25, the supply pipe 25c and the discharge pipe 25d of supplying and discharging water W are arranged separately on both sides in the width direction of the transfer belt 25, the invention is not limited thereto. FIG. 8 through FIG. 10 show modified examples of the embodiment. According to a first modified example shown in FIG. 8, the supply pipe 25c is arranged at substantially a center in the width direction on a lower side of the transfer belt 20, and the discharge pipes 25d are respectively arranged on both sides in the width direction of the transfer belt 20. According to the modified example, a distance in the width direction of the transfer belt 20 from supply to discharge of the liquid storing portion 18 can be shortened by arranging the supply pipe 25c and the discharge pipes 25d as described above. Therefore, the liquid can be supplied and discharged swiftly in the width direction of the transfer belt 20, and the transfer belt 20 can be brought into the wet state further uniformly in the width direction by the supplying and discharging means 25. Further, by arranging the supply pipe 25c at the position proximate to the transfer belt 20, water W can further firmly be spread in the range of arranging the transfer belt 20.

Further, according to a second modified example shown in FIG. 9, the supply pipes 25c are respectively arranged on the both sides in the width direction of the transfer belt 20, and the discharge pipe 25d is arranged substantially at the center in the width direction on the lower side of the transfer belt 20. Further, also in the modified example, similar to the first modified example, a distance in the width direction of the transfer belt 20 from supply to discharge can be shortened in the liquid storing portion 18. Therefore, supply and discharge of the liquid can swiftly be carried out in the width direction of the transfer belt 20, and the transfer belt 20 can be brought into the wet state further uniformly in the width direction by the supplying and discharging means 25.

Further, according to a third modified example shown in FIG. 10, both of the supply pipe 25c and the discharge pipe 25d are arranged substantially at the center in the width direction on the lower side of the transfer belt 20. Further, according to the modified example, by being arranged as described above, water W can further firmly be spread and discharged within the range of arranging the transfer belt 20.

Second Embodiment

Figure 11:
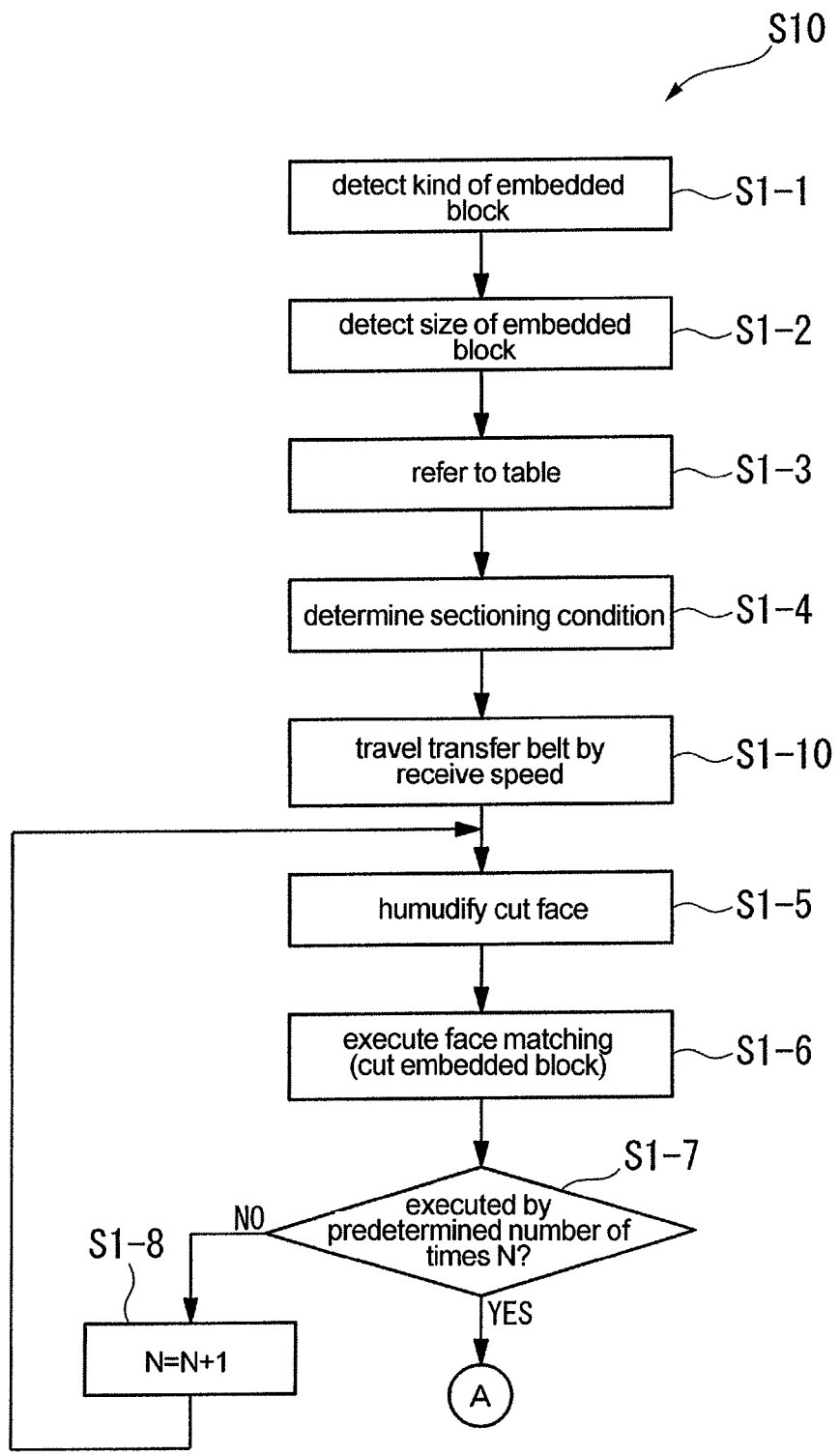
FIG. 11 is a flowchart showing details of preparing steps in making a thin-section by using a thin-section manufacturing apparatus according to a second embodiment of the invention.
Figure 12:
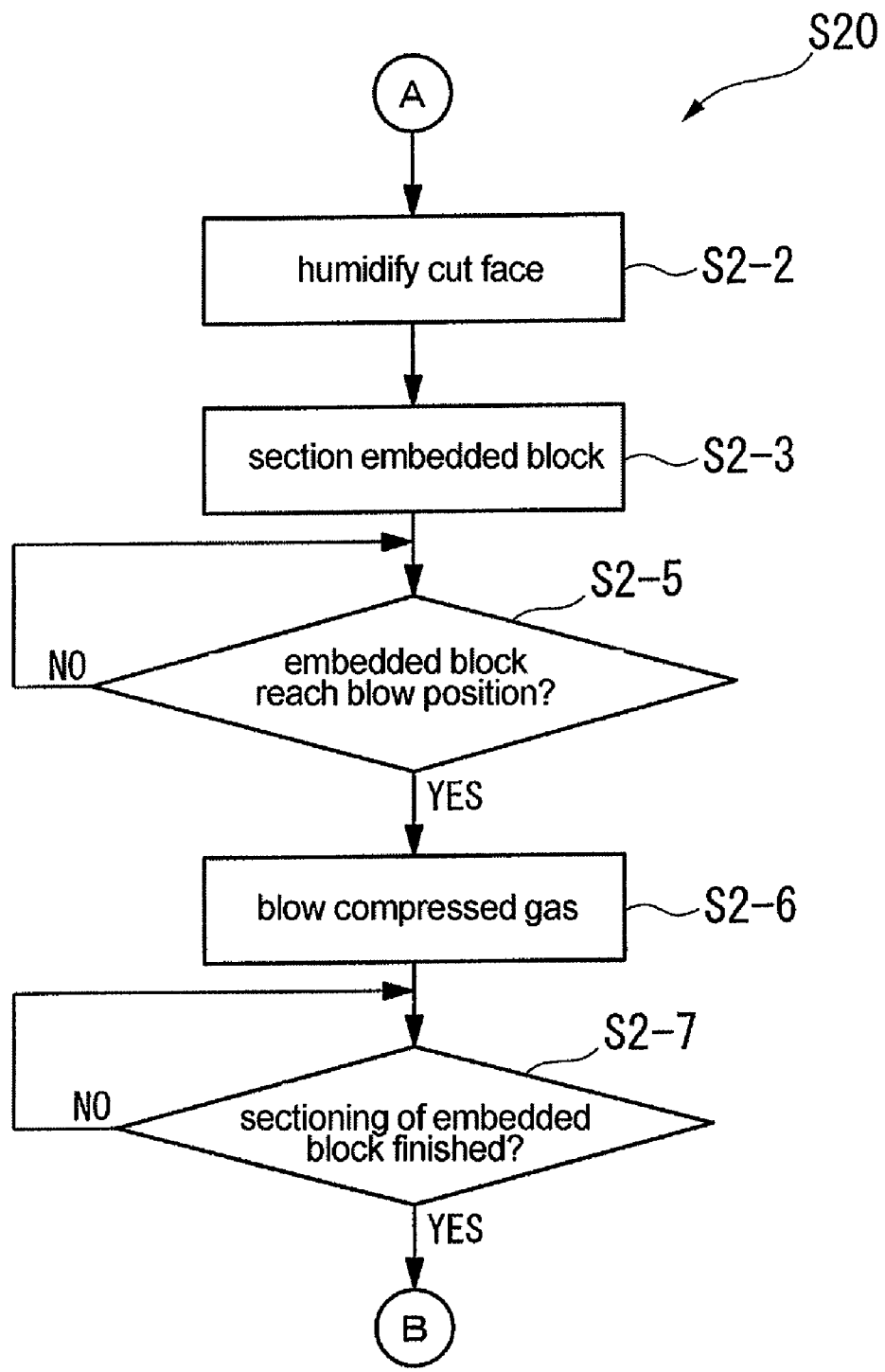
FIG. 12 is a flowchart showing details of thin-section manufacturing steps in making the thin-section by using the thin-section manufacturing apparatus according to the second embodiment of the invention.
Figure 13:
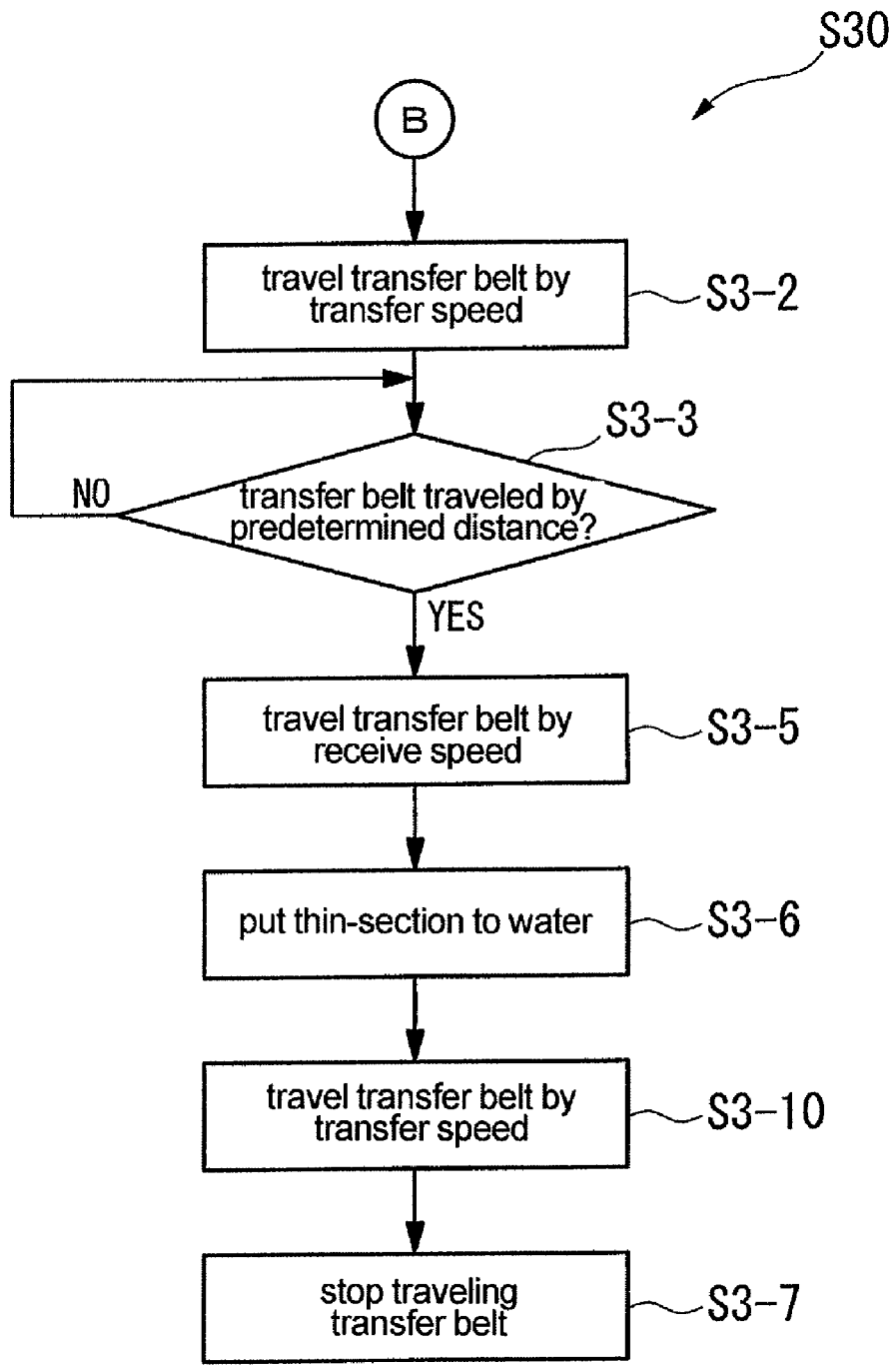
FIG. 13 is a flowchart showing details of transferring steps in making the thin-section by using the thin-section manufacturing apparatus according to the second embodiment of the invention.

Next, a second embodiment of the invention will be explained. FIG. 11 through FIG. 13 show a second embodiment of the invention. Further, according to the embodiment, there is constructed a constitution similar to that of the thin-section manufacturing apparatus 1 of the first embodiment except that the supplying and discharging means 25 is not provided and that a control flow by the controller 7 partially differs, and therefore, a total view of the apparatus will be omitted, and an explanation will be given in reference to FIG. 1. An explanation will be given as follows by centering on a point which differs from the first embodiment in the flow of making and transferring the thin-section.

That is, as shown by FIG. 11, according to a thin-section manufacturing apparatus of the embodiment, at preparing step S10, the controller 7 determines the sectioning conditions at step S1-4, thereafter, travels the transfer belt 20 by the receive speed by driving the transfer drive portion 22 as step S1-10, thereafter, carries out face matching at steps S1-5 through S1-7. Here, by previously traveling the transfer belt 20, and making the speed by the receive speed of a low speed, the transfer belt 20 passing water W of the liquid bath 6 is transferred to the first turn back portion 20a while including water W. Further, by turning back the transfer belt 20 from a lower side to an upper side at the first turn back portion 20a, water W transferred from the liquid bath 6 by the transfer belt 20 is dropped and is stored at the liquid storing portion 18. Therefore, the liquid storing portion 18 can be filled with water W by repeatedly traveling the transfer belt 20 while carrying out face matching, and the transfer belt 20 can maintain preferably the wet state by water W stored at the liquid storing portion 18 by the transfer belt 20 per se. Therefore, at thin-section manufacturing step S20, as shown by FIG. 12, the thin-section B1 which is made can firmly be received by the transfer belt 20 at the receive position P without positively supplying water W to the liquid storing portion 18.

Further, as shown by FIG. 13, according to the embodiment, the thin-section B1 is delivered to water W of the liquid bath 6 as step S3-6, thereafter, the transfer belt 20 is traveled again by the transfer speed for predetermined time as step S3-10. Here, by traveling the transfer belt 20 by the transfer speed faster than the receive speed, an amount of water W stirred up from the liquid storing portion 18 on the upper side of the first turn back portion 20a becomes larger than an amount of water W transferred from the liquid bath 6 to the liquid storing portion 18 on the lower side of the second turn back portion 20b by the transfer belt 20. Therefore, water W of the liquid storing portion 18 can be discharged by continuing to travel the transfer belt 20 for the predetermined time. Further, when the execution of step S3-10 is finished, the controller 7 proceeds to step S3-7, and finishes the operation by stopping to travel the transfer belt 20. Further, an end of the execution at step S3-10 is judged by determining whether traveling of the transfer belt 20 is carried out for the predetermined time by the controller 7 based on the result of measurement by the timer 28 by previously setting sufficient time for discharging water W of the liquid storing portion 18.

As described above, according to the embodiment, by adjusting the traveling and the speed of the transfer belt 20, the amount of water W of the liquid storing portion 18 can be adjusted, the supplying and discharging means 25 can be omitted, and therefore, low cost formation can be achieved by simplifying the constitution. Further, although in the above-described, in supplying water W to the liquid storing portion 18, the transfer belt 20 is set to the receive speed and when water W is discharged from the liquid storing portion 18, the transfer belt 20 is set to the transfer speed, the invention is not limited thereto. At step S1-10 shown in FIG. 11, when the receive speed is a speed slower than a speed of balancing incomings and outgoings of the amount of water W transferred from the liquid bath 6 and the amount of water W stirred up from the liquid storing portion 18, the amount of water W transferred from the liquid bath 6 becomes larger, and water W can be supplied to the liquid storing portion 18. Further, at step S3-10 shown in FIG. 13, when the transfer speed is a speed faster than the above-described balanced speed, the amount of water W stirred up from the liquid storing portion 18 becomes larger, and water W can be discharged from the liquid storing portion 18. Further, even when the receive speed and the transfer speed do not comply with the above-described condition, naturally, the speeds in supplying and discharging water W to and from the liquid storing portion 18 are set to speeds different from the receive speed and the transfer speed.

Although a detailed description has been given of the embodiments of the invention in reference to the drawings as described above, a specific constitution is not limited to the embodiments but a design change or the like within the range not deviated from the gist of the invention is also included.

What is claimed is:

1. A thin-section manufacturing apparatus comprising:
   a cutter sectioning an embedded block;
   a cutter fixing portion including a fixing base supporting the cutter, and a cutter holder squeezing the cutter from an upper side to the fixing base;
   a sample base fixing the embedded block;
   feeding means for moving the sample base relative to the cutter in a predetermined feeding direction and sectioning the embedded block by the cutter;
   a liquid bath arranged on a rear side of a cut edge of the cutter and holding a liquid; and
   a transfer belt in an endless loop having a first turn back portion provided on an upper side of the cutter and a second turn back portion provided at an inner portion of the liquid bath and transferring a thin-section sectioned from the embedded block to the liquid bath;
   wherein an upper face of the cutter holder includes a liquid holding portion that contains a portion of the liquid, the liquid holding portion having a wall face inclined upward from the cutter in a direction substantially aligned with the transfer belt;
   wherein the first turn back portion of the transfer belt is arranged at an inner portion of the liquid holding portion; and
   wherein a distance between the first turn back portion of the transfer belt and the wall face of the liquid holding portion is such that an inclined liquid surface is formed by surface tension that extends from an upper end of the wall face to a surface of the transfer belt and the distance is such that the thin-section is simultaneously supported against the wall face, the liquid surface, and the transfer belt.

2. The thin-section manufacturing apparatus according to claim 1, wherein the liquid holding portion includes supplying and discharging means for supplying and discharging the liquid.

3. The thin-section manufacturing apparatus according to claim 2, wherein the supplying and discharging means includes a supply pipe for supplying the liquid and a discharge pipe for discharging the liquid; and
   wherein one of the supply pipe and the discharge pipe is arranged substantially at a center in a width direction of the transfer belt, and the other thereof includes two pipes respectively arranged on both sides of the transfer belt in the width direction of the transfer belt.

4. The thin-section manufacturing apparatus according to claim 2, further comprising:
   a control portion for supplying a previously set necessary amount of the liquid to the liquid holding portion by the supplying and discharging means in accordance with sectioning conditions of the embedded block including the moving rate of the sample base relative to the cutter, and discharging the liquid from the liquid holding portion by the supplying and discharging means for a time interval determined by the transfer of the thin-section from the liquid holding portion to the liquid bath.

5. The thin-section manufacturing apparatus according to claim 1, wherein the liquid in the liquid holding portion of the cutter holder comprises a liquid including water, and a bottom face of the liquid holding portion comprises a hydrophilic surface.

6. The thin-section manufacturing apparatus according to claim 1, wherein the liquid in the liquid holding portion of the cutter holder comprises a liquid including water, and the wall face surrounding the liquid holding portion comprises a hydrophobic surface.

* * * * *